US00PP07882P

United States Patent [19]

Turner, Sr.

[11] Patent Number: Plant 7,882

[45] Date of Patent: * Jun. 9, 1992

[54] *MERIUM OLEANDER* PLANT—TURNER'S KATHRYN CHILDERS

[76] Inventor: Ted L. Turner, Sr., 6503 S.P.I.D., Corpus Christi, Tex. 78412

[ * ] Notice: The portion of the term of this patent subsequent to Apr. 9, 2009 has been disclaimed.

[21] Appl. No.: 519,297

[22] Filed: May 4, 1990

[51] Int. Cl.[5] ..... A01H 5/00

[52] U.S. Cl. ..... Plt./54

[58] Field of Search ..... Plt./54

[56] References Cited

U.S. PATENT DOCUMENTS

P.P. 5,378 12/1984 Turner ..... Plt. 54
P.P. 6,339 10/1988 Turner ..... Plt. 54
P.P. 7,619 8/1991 Turner ..... Plt. 54

*Primary Examiner*—James R. Feyrer
*Attorney, Agent, or Firm*—Stewart N. Rice

[57] ABSTRACT

A *Nerium oleander* plant which has an intermediate and upright habit of fairly rapid growth, being particularly characterized by its everblooming character and the unique color of its inflorescence, the flowers being white with a soft pink blush or tint.

1 Drawing Sheet

DESCRIPTION OF THE INVENTION

The present invention relates to a new and distinct variety, of intermediate size, of *Nerium oleander* which was originated by me as a seedling by selection and crossing. I crossed a *Nerium oleander* "Algiers" with a *Nerium oleander* "Turner's Carnival". The "Algiers" is an intermediate size plant which produces a single flower of florescent red color. The intermediate size of oleander is slightly smaller than the standard size but larger than the dwarf and petite sizes. "Turner's Carnival" is the subject of U.S. Plant Pat. No. 6,339 issued Oct. 18, 1988 by Ted L. Turner, Sr., and this plant is a petite size plant with soft pink flowers. However in making my crosses, I observed that pollination could have been accomplished by bees from unkown plants. Thus unknown parentage could have been introduced by the bees even though I did not purposely introduce any parentage other than the "Turner's Carnival" and the "Algiers".

From the group of seedlings I observed a plant. being the plant claimed herein, having a new and distinct color of flowers, and from cuttings of such plant I was able to asexually reproduce plants having the same characteristics and flow color as the original seedling. All of the descendant plants showed the same characteristics as the original seedling, and as a result of extensive observations and tests which are not described in full herein for sake of brevity, it is my opinion and I am convinced that my new plant is a new variety of *Nerium oleander* which is distinguished from all other varieties of which I am aware as evidenced by the following unique combination of principal characteristics which are outstanding therein:

(1) An upright habit of fairly rapid growth and of intermediate size making it especially suitable for use as a screening plant or to add garden color;

(2) An ability to be asexually reproduced;

(3) An everblooming ability to flower substantially throughout the year;

(4) The ability to bloom in partial shade, such as morning sun only; and (5) The ability to be a good greenhouse bloomer; and (6) The ability to produce a flower having a white color with a soft pink blush.

Asexual reproduction of my new variety as by cuttings shown that the foregoing characteristics and distinctions come true to form and are established and transmitted through succeeding propagations.

The accompanying FIGURE is a photograph of a typical flower on the plant of my new variety more clearly illustrating the colors present on each flower. The true color of the foliage and flowers is described in the following description and is depicted in the FIGURE which depicts the color as nearly as true as is reasonably possible in a color illustration of this type.

The following is a detailed description of my new variety of *Nerium oleander,* which color numbers in accordance with the Pantone Matching System of colors for printing inks, Pantone Color Formula Guide 747×R, 1987–1988, published by Pantone, Inc. Terms used to describe colors are those of ordinary significance.

The Plant

Growth habit: Upright, intermediate size; the height of an unpruned mature plant will probably be from about 3 to 6 meters, but has not yet been determined; fast growing. The plant grows full from just about ground level upward, with the width of the plant about 40% to 65% of the height.

Hardiness: Adapted to seaside planting as it tolerates soil with relatively high salt content; tolerates droughts; will not withstand prolonged and severe freezing weather; most suitable for the Southern United States from California to Florida, in the areas known as Zones 9 and 10; withstands heat and light and grows either in full sun or in partial shade (up to 50% shade) such as morning sun only.

Branches: The plant is loosely branched from just above ground level with main branches and branchlets ascending. The plant does not develop a central leader or trunk. New growth of branches is a light to medium green, Color No. 391U, changing to light greenish brown, Color No. 4505U, in color as branches mature.

Blooming period: In a mild winter, an outside plant will bloom off and on substantially the entire year. In a cold winter, an outside plant will bloom off and on about 80% of the year. The plant will bloom substantially all the time in a greenhouse.

The Foliage

Type: Broadleaf evergreen; numerous; petioled; grow in a whorl with three leaves in each whorl.

Shape: Linear-lanceolate, with entire margins. Apex is more or less acuminate and slightly non-symmetrical, and base is acute.

Petioles: Length, from about 8 to 10 mm; color pale green.

Leaf size: Length of mature leaf from about 180 to 210 mm; width of mature leaf about 25 to 35 mm. Size of leaf varies according to sunshine conditions at the time the leaf is produced, with larger leaves being produced under cloudy conditions than under sunny conditions.

Venation: Midrib or under surface prominent and readily apparent and is pale green, Color No. 586U; on upper surface midrib is clearly visible and slightly recessed, and is pale green, Color No. 586U; lateral veins are not readily apparent on upper surface but under surface contains numerous, delicate, almost parallel lateral veins which are readily apparent, the lateral veins being substantially perpendicular to the midrib.

Leaf color:

Mature leaves.—Upper surface — dark green, Color No. 574C; under surface much lighter in color than upper surface, being a pale green, Color No. 5767U.

New leaves.—Slightly lighter in color than mature leaves.

Leaf texture: Tough, leathery; smooth; upper surface — semi-glossy; lower surface — dull.

The Inflorescence

Position and abundance: Flowers cluster at twig or branch ends in terminal cymes, with cymes appearing at various positions from the lower part to the upper part of the plant.

Form: Single; regular; pediceled; petals united in a sympetalous corolla; salverform; tube spreads into five limbs or lobes; each flower is about 38 to 45 mm across; corona conspicuous at junction of tube and spreading limb, corona about 10 to 15 mm in diameter and much shorter than spreading limbs, the corona having five crownlike appendages, each appendage corresponding to a limb, most appendages being 2 to 4 toothed;

Buds: Limbs convolute in the bud, obliquely apiculate, the folds twisting counterclockwise when viewing down into the tip of the bud, such the limbs of the flower twist clockwise when viewing down into the flower.

Calyx: Of 5 persistant sepals, imbricate in the bud, lanceolate, acuminate, about 4 to 6 mm long.

Stamen: 5 stamens; filaments partly adnate to corolla tube; anthers with 2 basal tails, apex long-attenuate, hairy.

Color of flower: Limbs or petals of the corolla in new flowers are white with a very pale pink blush or tint, the pink of the blush being a very pale version of pink, Color No. 196C. Blooms produced under a full sun will be lighter in shade than those produced on cloudy days as is the case with most oleanders. As the flowers age, the color of the limbs fade becoming more pale than in the new growth. The upper portion of the corona is a very pale pinkish white, being slightly paler than Color No. 182C, with 5 groups of 3 dark pinkish red streaks, Color No. 185U, each group of pinkish red streaks being more or less centered with and corresponding to limb and to a said corona appendage, the streaks being radial in nature (as opposed to circular) such that the streaks extend from the edge of each appendage down into the corona tube, or vice versa. The color of the upper portion of the corona is a slightly darker shade than the color of the limbs or petals. The lower portion of the corona, not generally visible when viewing the flower, has tinges of pale yellow. The outside of the corolla tube of each flower is pale pink, Color No. 197C, with streaks of pinkish red, Color No. 190U, there being in particular 5 small pinkish red streaks extending along the tube alternate with the spreading limbs. The bottom of the corona tube is a pale golden, yellow, Color No. 114U. The calyx and sepals are pinkish red, Color No. 205U.

Color of buds: Light pink, Color No. 1765U.

To further describe my new variety of *Nerium oleander,* it is very similar in size and growth habit to the other well-known intermediate size *Nerium oleanders* which grow in an upright manner, except for the color of the flowers, and except that my new variety appears to tolerate shade better than the other intermediate *Nerium oleanders* of which I am aware. My new variety also blooms much earlier, and longer, than other standard *Nerium oleanders* of which I am aware and blooms more profusely with each cluster or terminal cyme appearing to have more blooms per cluster than prior art intermediates of which I am aware. I am not aware of any *Nerium oleander* of any size having a flower which is the same as that produced by my plant. My plant will make good small blooming trees and will also be good for pots and tubs.

VARIETY NAME

The proposed variety name of may new plant is *Nerium oleander* "Turner's Kathryn Childers".

I claim:

1. A new and distinct variety of intermediate size *Nerium oleander* substantially as shown and described, having an upright habit of fairly rapid growth making it especially suitable as a screening plant, having an ability to be asexually reproduced, having the ability to flower off and on throughout the entire year, having the ability to grow in full sun or in partial shade, being an excellent greenhouse plant, and being particularly characterized by its intermediate size combined with the unique color of its inflorescence, the flowers being white with a very pale pink blush or tint.

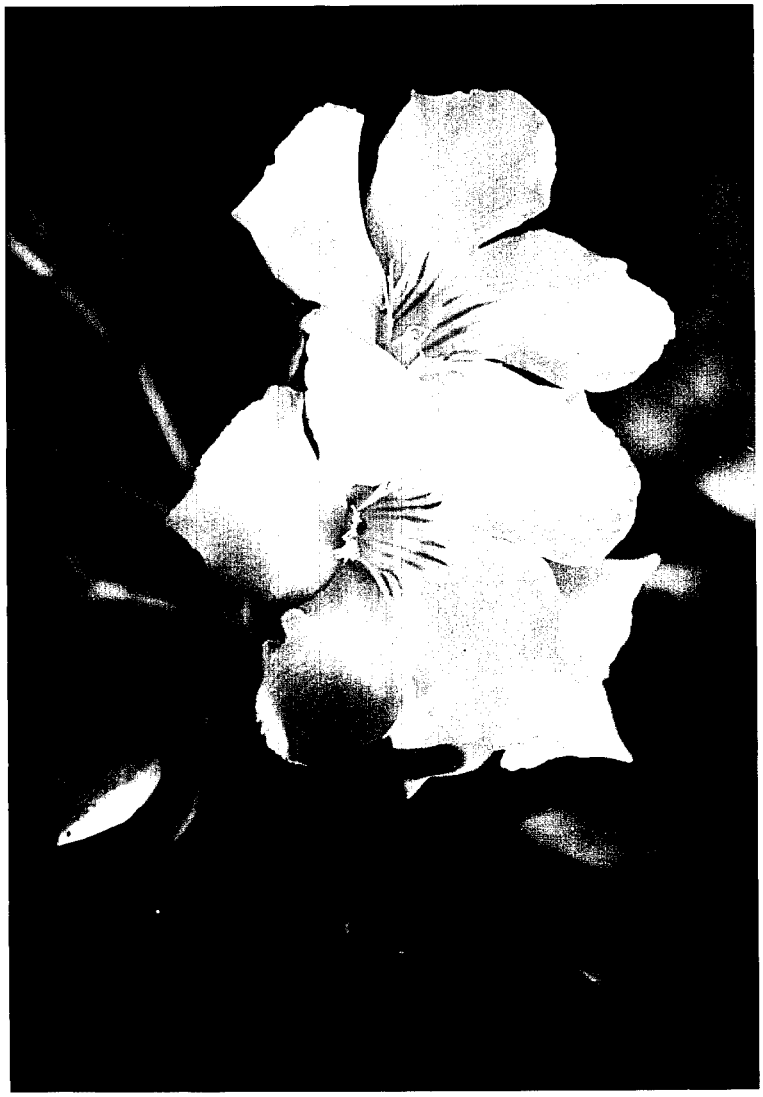

* * * * *